United States Patent
Hokanson

(10) Patent No.: US 9,168,064 B2
(45) Date of Patent: Oct. 27, 2015

(54) BILATERAL DYNAMIC EXTERNAL DISTRACTOR FOR THE TREATMENT OF COMPLEX FRACTURE LUXATIONS OF THE PROXIMAL INTERPHALANGEAL JOINT OF THE HAND

(71) Applicant: Ellen Hokanson, Woods Hole, MA (US)

(72) Inventor: Charles Hokanson, Woods Hole, MA (US)

( * ) Notice: Subject to any disclaimer, the term of this patent is extended or adjusted under 35 U.S.C. 154(b) by 0 days.

(21) Appl. No.: 13/938,714

(22) Filed: Jul. 10, 2013

(65) Prior Publication Data
US 2014/0025075 A1    Jan. 23, 2014

Related U.S. Application Data

(60) Provisional application No. 61/672,540, filed on Jul. 17, 2012.

(51) Int. Cl.
| | | |
|---|---|---|
| A61B 17/00 | (2006.01) | |
| A61B 17/66 | (2006.01) | |
| A61B 17/64 | (2006.01) | |

(52) U.S. Cl.
CPC ............. *A61B 17/66* (2013.01); *A61B 17/6441* (2013.01)

(58) Field of Classification Search
CPC ........ A61B 17/56; A61B 17/58; A61B 17/60; A61B 17/64; A61B 17/6408; A61B 17/6416; A61B 17/6425; A61B 17/6433; A61B 17/6441; A61B 17/645; A61B 17/6458; A61B 17/6466; A61B 17/6475; A61B 17/6483; A61B 17/6491; A61B 17/66; A61B 17/68; A61B 17/681; A61B 17/686
USPC ............................... 606/32, 54–59, 72, 73, 90
See application file for complete search history.

(56) References Cited

U.S. PATENT DOCUMENTS

| | | | |
|---|---|---|---|
| 4,100,919 A | 7/1978 | Oganesyan et al. | |
| 4,548,199 A | 10/1985 | Agee | |
| 4,604,997 A | 8/1986 | De Bastiani et al. | |
| 4,724,827 A | 2/1988 | Schenck | |
| 4,730,608 A * | 3/1988 | Schlein | 606/57 |
| 5,129,904 A * | 7/1992 | Illi | 606/304 |
| 5,376,091 A | 12/1994 | Hotchkiss et al. | |
| 5,505,733 A * | 4/1996 | Justin et al. | 606/63 |
| 5,976,125 A * | 11/1999 | Graham | 606/32 |
| 7,473,256 B2 * | 1/2009 | Assell et al. | 606/90 |

(Continued)

FOREIGN PATENT DOCUMENTS

WO    WO2006125883    11/2006

*Primary Examiner* — Jerry Cumberledge
*Assistant Examiner* — Tessa Matthews
(74) *Attorney, Agent, or Firm* — Buckingham, Doolittle & Burroughs, LLC

(57) ABSTRACT

A bilateral dynamic external distractor is disclosed for the treatment of complex fracture luxations of the PIP of the hand. The distractor comprises two setscrews, one left proximal guide block, one right proximal guide block, two threaded rods, two distal guide blocks, and two optional alignment guide clips. The left and right distal guide blocks each comprise a threaded passage, and the first threaded rod extends between the right proximal guide block and the right distal guide block, and the second threaded rod extends between the left proximal guide block and the left distal guide block. Furthermore, rotation of the first and second threaded rods causes the left and right distal guide blocks to move relative to the left and right proximal guide blocks along an axis of the first and second threaded rods.

13 Claims, 11 Drawing Sheets

(56) References Cited

U.S. PATENT DOCUMENTS

| | | |
|---|---|---|
| 2006/0149165 A1* | 7/2006 | Kennedy et al. ............... 600/585 |
| 2007/0038217 A1* | 2/2007 | Brown et al. .................. 606/57 |
| 2009/0054897 A1* | 2/2009 | Gordon et al. .................. 606/57 |
| 2012/0143191 A1* | 6/2012 | Foote ............................. 606/59 |
| 2013/0296858 A1* | 11/2013 | Hollawell ....................... 606/59 |

* cited by examiner

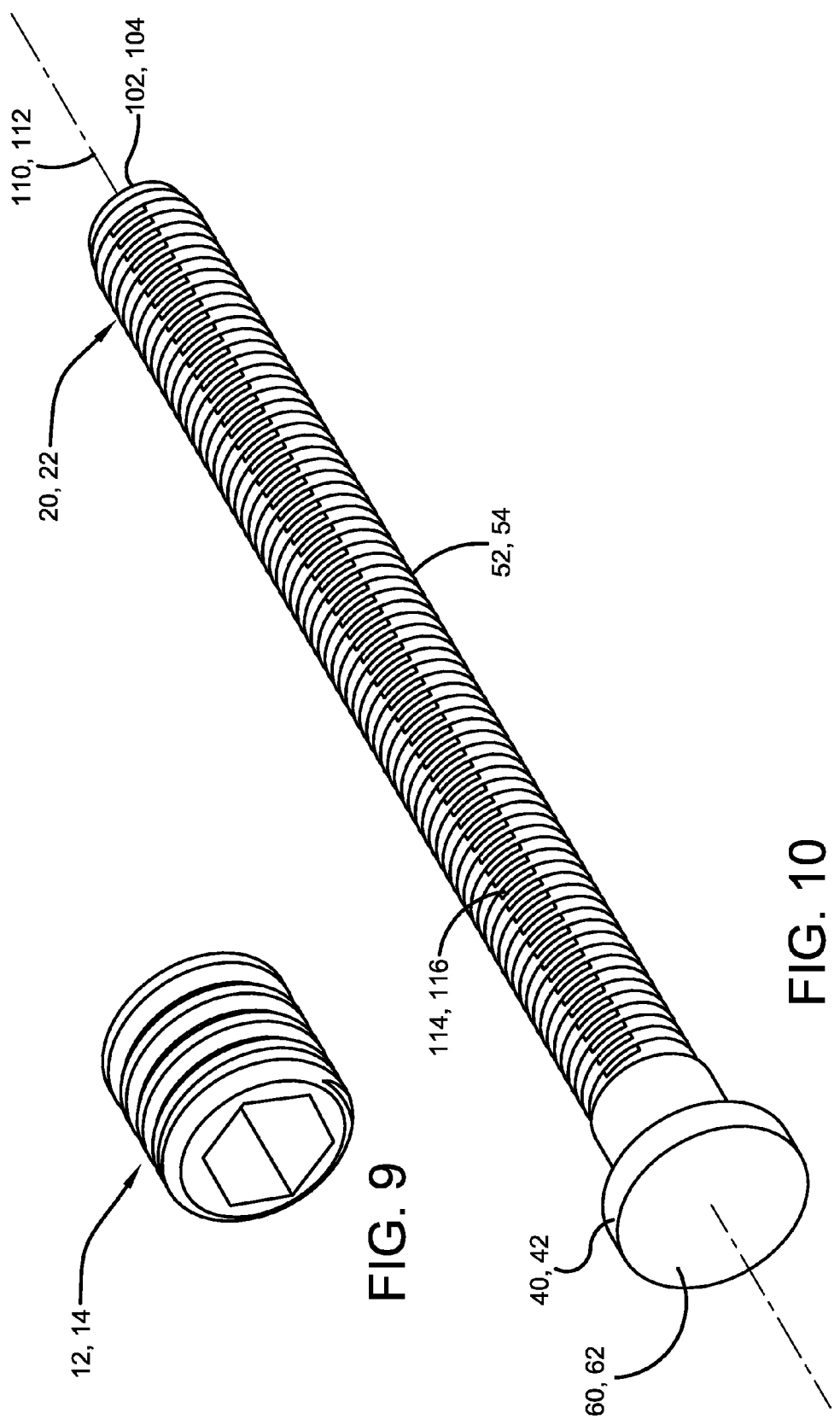

BILATERAL DYNAMIC EXTERNAL DISTRACTOR FOR THE TREATMENT OF COMPLEX FRACTURE LUXATIONS OF THE PROXIMAL INTERPHALANGEAL JOINT OF THE HAND

CROSS-REFERENCE

This application claims priority from Provisional Patent Application Ser. No. 61/672,540 filed Jul. 17, 2012.

BACKGROUND

Fracture dislocation of the Proximal Interphalangeal Joint (PIP) is a common injury of the digits of the hand. The principle of traction to treat a fracture is a relatively old idea, but the concept of movement is relatively new. In 1978, Oganesyan described an apparatus for the treatment of intra-articular fractures, with simultaneous movement, see U.S. Pat. No. 4,100,919. The device was constructed of at least two wires drawn through bones on either side of the affected joint. These wires were rigidly connected to arches, which externally bridge the affected bones, creating a rigid construct. A key feature of this device was a threaded rod designed to alter the distance between the wires, and the bone segments attached thereto. The purpose of the distraction was to increase the distance between the bones at the axis or rotation of the joint, in order to promote healing and preserve the cartilage at the joint during active motion. The traction applied to the articulation not only aimed to re-focus the skeleton but also to generate a force of distal distraction. This distraction offers several beneficial effects. First, it allows the reduction of articular fragments and restoration of continuity by drawing on their joint ligament attachments and the volar plate, via the process of ligamentotaxis. Maintaining this tension allows distal fragments to remain in place during healing. Secondly, the distraction force prevents retraction of distal capsulolabral structures. Further, joint mobilization improves cartilage regeneration and healing. The combined results of these two methods are anatomic restoration of joint function, all without invasive surgery.

Then in 1986, Schenck introduced this technique to the field of hand surgery, see U.S. Pat. No. 4,724,827. Schenk described an apparatus to treat fracture luxations of the PIP with dynamic traction. His device involved passage of a K-wire transversely through the phalanges distal to P2, and attaching elastic bands to a rigid arc surrounding the digit. The elastic bands created a stretching force of 300 grams, and the device permitted passive motion of the digit. Patients treated with this device responded well to the treatment with little loss of range of motion and none of the complications related to the open reduction procedures, which had been the standard of care up until this innovation. However, the device was cumbersome and complicated and as such it was not well accepted in the surgical community.

In 1986, De Bastiani described a unilateral articulated mini fixation device, see U.S. Pat. No. 4,604,997, which was comprised of a hinge between two blocks, which may be attached to bone segments proximal and distal to the PIP. A threaded adjustment rod is included to provide longitudinal displacement between the blocks.

Then in 1987, Agee described a device for the treatment of unstable fracture luxations of the PIP, see U.S. Pat. No. 4,548,199. The Agee device was based upon placement of two K-wires placed proximal and distal to the PIP. A bone screw was drilled into the ulnar surface of the middle phalanx distal to the PIP, and attached to elastic bands stretched across vertical risers on the K-wire, on either side of the digit, proximal to the PIP. The device provided some degree of distraction of the PIP. It also permitted limited passive and active mobilization of the digit. However, the device was not well tolerated by patients due to its cumbersome design. In addition, the bone screw through the ulnar surface of the phalanges could result in damage to the extensor tendon. As a consequence, the surgical community did not adopt this technique.

Between 1987 and 1993, surgeon inventors described several other devices in an effort to improve the treatment of fracture luxations of the PIP. Most of these devices were complicated and cumbersome, and none were widely accepted in the surgical community.

In 1994, Hotchkiss described dynamic joint support, see U.S. Pat. No. 5,376,091. The invention provided for proximal and distal support sections and means for rigidly connecting each support section to bone and a pair of hinges connecting each support section to each other. Further, the device provided pivoting at the joint to cause movement of the support section and its corresponding attached bone through the movements of flexion and extension. The hinge was driven in its movement by a threaded worm gear mechanism. The dynamic joint support included a threaded rod distraction mechanism for movement of the bones out of contact in the joint, allowing for an active range of motion at the joint. While providing improved clinical results, the device proved expensive to manufacture and cumbersome to use and was subsequently discontinued.

In 1994, Suzuki described a low profile system, which seemed to solve many of the issues related to previous designs. The Suzuki system involved placement of K-wires, one proximal and one distal to the PIP. Results using the operating room constructed Suzuki technique have proven to be better than previous methods. However, patient outcome varies significantly with surgeon skill and experience. The Suzuki technique has a significant learning curve to master the shape and length of the wires. And, care must be exercised to avoid side loading damage to the bones, while bending the wire. In addition, movement of the proximal wire within the bone during passive and active motion can result in an increase in pin tract infection. Furthermore, the device was limited to 30 degrees of flexion, and distraction force varied greatly depending upon the rubber bands available and the length of the physician created device. This limited range of flexion resulted clinically in an average range of motion of only 74 degrees.

In 1999, Graham described a device for treatment of fracture dislocations of the interphalangeal joints, see U.S. Pat. No. 5,976,125. This apparatus required assembly of a series of components including proximal and distal fixators, proximal and distal guide rods, and adjustable threaded distraction rods. By assembling the fixators contralaterally with their respective guide rods and ipsilaterally with respect to their distraction rods, a rigid rectangular construct is formed, through which K-wires may be drilled proximal and distal to the PIP. Placement of the proximal K-wire at the center of the axis of rotation of the PIP, and perpendicular to the PIP, is critical to the optimal functioning of dynamic distraction. Unfortunately, this is difficult to accomplish while holding the construct over the PIP, and frequently results in an off center, or angled K-wire placement with respect to the plane perpendicular to the longitudinal axis of the PIP. Furthermore, this technique is contrary to the traditional surgical technique of wire placement before attachment of the distraction device. The Graham device can be assembled subsequent to wire placement, however this further complicates the procedure due to the number of setscrews, clips, rods, and stabilizers required for assembly. A further disadvantage of this device is that adjustment of the distraction rods is accomplished with an Allen wrench. This can lead to excess distraction force resulting in stress or failure of the digital ligament. Further, no provision is made to lock the distraction rod in place and prevent it from unwinding once optimum distraction has been achieved. In addition, there is no provision to prevent ulnar or palmar luxation of the phalanges, a frequent complication of distraction devices. Finally, due to its complicated design, the device is expensive to manufacture, and bulky to utilize, therefore it has not achieved wide spread use among hand surgeons.

In 2006, Pélissier of France disclosed a simple, low profile device for ligamentotaxis of the PIP (see EP 1898815). His device consisted of two springs, and two grommets held in place by two longitudinal wires. Each longitudinal wire was placed in the lumen of each spring. Once the K-wires were placed at the axis of rotation of the PIP and a point distal to the PIP, the distal wire is bent at a right angle on either side of the digit, and cut to a length approximately equivalent to half the distance between the proximal and distal wires. The open end of each spring is then slipped over the right angle sections of the distal K-wire, and the proximal wire is passed through the grommet at the opposite end of the spring. The proximal wires may then be bent and capped to retain the springs in place on either side of the affected digit. Distraction is accomplished by clockwise rotation of the springs. While the Pélissier device was an improvement over previous designs, this device has one serious disadvantage; the metal springs are placed on either side of the digit, preventing radiographic confirmation of articular distraction in the lateral view.

The novel device herein presented, addresses the deficiencies identified in the above-recited prior art and provides an improved dynamic external distractor for the treatment of complex fracture luxations of the PIP of the hand. The device provides a simple, low cost solution for the treatment of fracture dislocations of the PIP. Further, the device permits standardization of treatment, by enabling surgeons to determine distraction forces, an important treatment parameter, which heretofore was impossible due to the limitations of the above-described prior art devices. Additionally, standardization will permit better patient outcomes than currently possible with existing systems.

All references cited herein are incorporated herein by reference in their entireties.

SUMMARY

The following presents a simplified summary in order to provide a basic understanding of some aspects of the disclosed innovation. This summary is not an extensive overview, and it is not intended to identify key/critical elements or to delineate the scope thereof. Its sole purpose is to present some concepts in a simplified form as a prelude to the more detailed description that is presented later.

The subject matter disclosed and claimed herein, in one aspect thereof, comprises a bilateral dynamic external distractor for the treatment of complex fracture luxations of the PIP of the hand. The distractor comprises two setscrews, one left proximal guide block, one right proximal guide block, two threaded rods, two distal guide blocks, and two optional alignment guide clips. The left and right distal guide blocks each comprise a threaded passage, and the first threaded rod extends between the right proximal guide block and the right distal guide block, and the second threaded rod extends between the left proximal guide block and the left distal guide block.

Furthermore, in a preferred embodiment, a first wire extends between the left and right proximal guide blocks, and a second wire extends between the left and right distal guide blocks. Additionally, rotation of the first and second threaded rods causes the left and right distal guide blocks to move relative to the left and right proximal guide blocks along an axis of the first and second threaded rods.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and is intended to include all such aspects and their equivalents. Other advantages and novel features will become apparent from the following detailed description when considered in conjunction with the drawings.

BRIEF DESCRIPTION OF THE DRAWINGS

FIG. 9 shows multiple views of a set screw of the distractor of FIG. 1.

FIG. 10 shows two views of a threaded rod of the distractor of FIG. 1.

DESCRIPTION OF PREFERRED EMBODIMENTS

Figure 1:
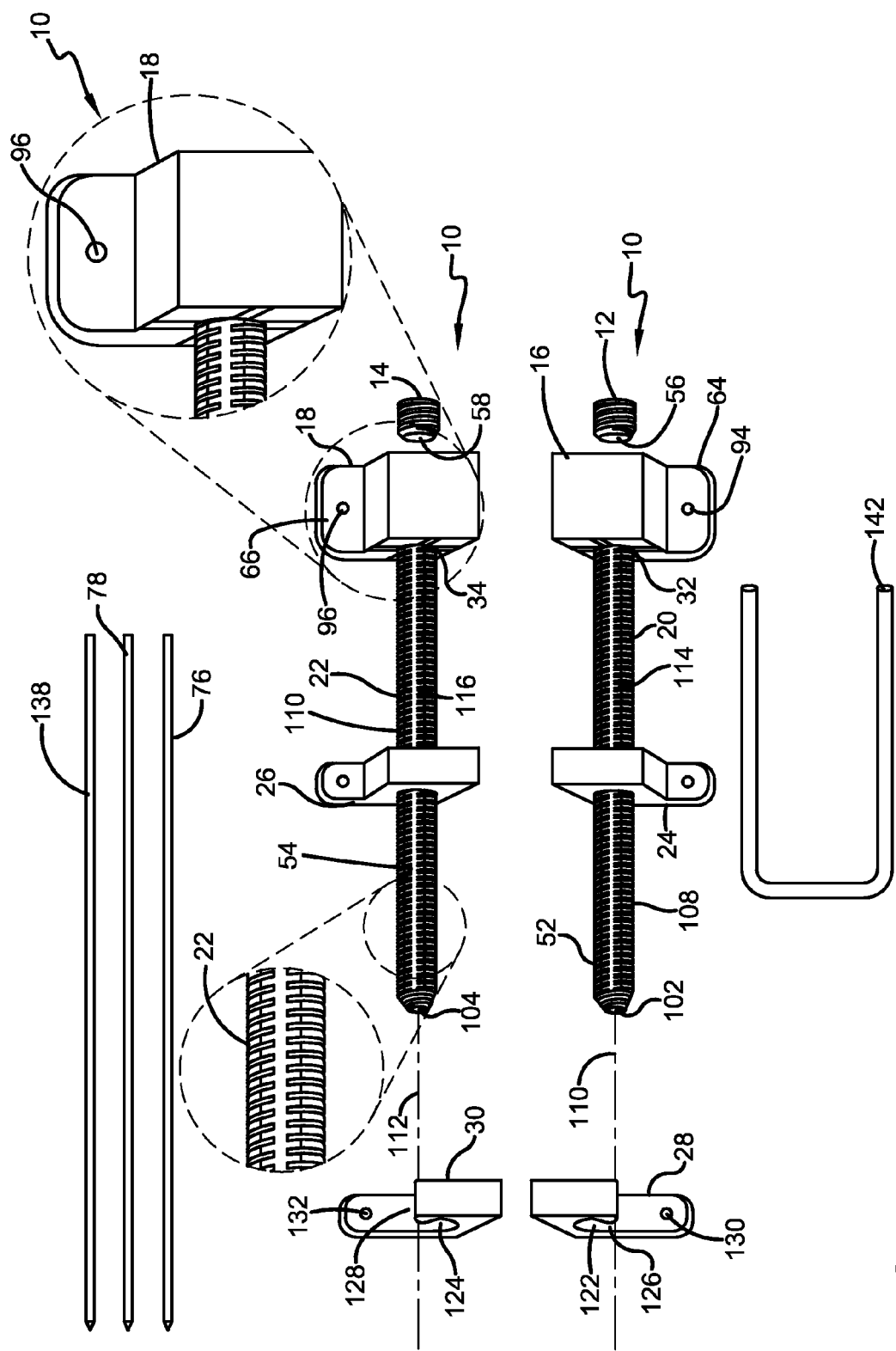
FIG. 1 is an exploded view of a bilateral distractor in accordance with an exemplary embodiment of the present invention.
Figure 2:
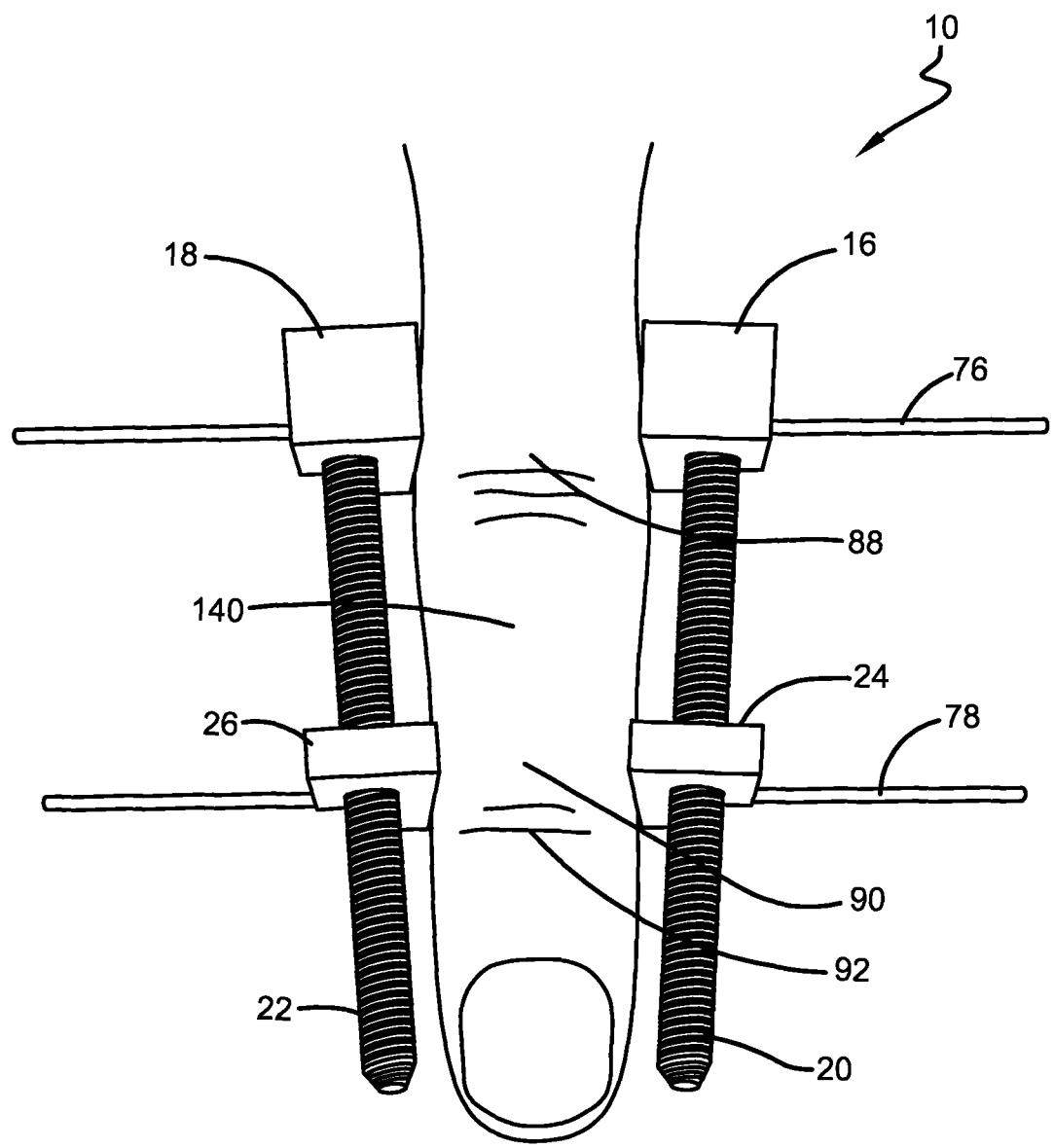
FIG. 2 is a top view of the distractor of FIG. 1, as attached to a finger.
Figure 3:
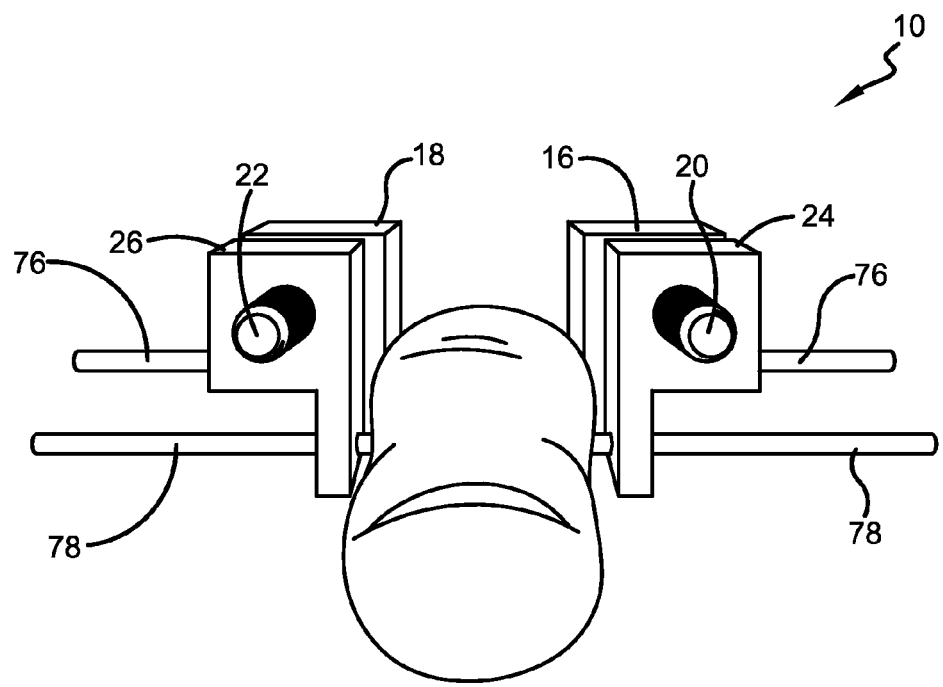
FIG. 3 is a front perspective view of the distractor of FIG. 1, as attached to a finger.
Figure 4:
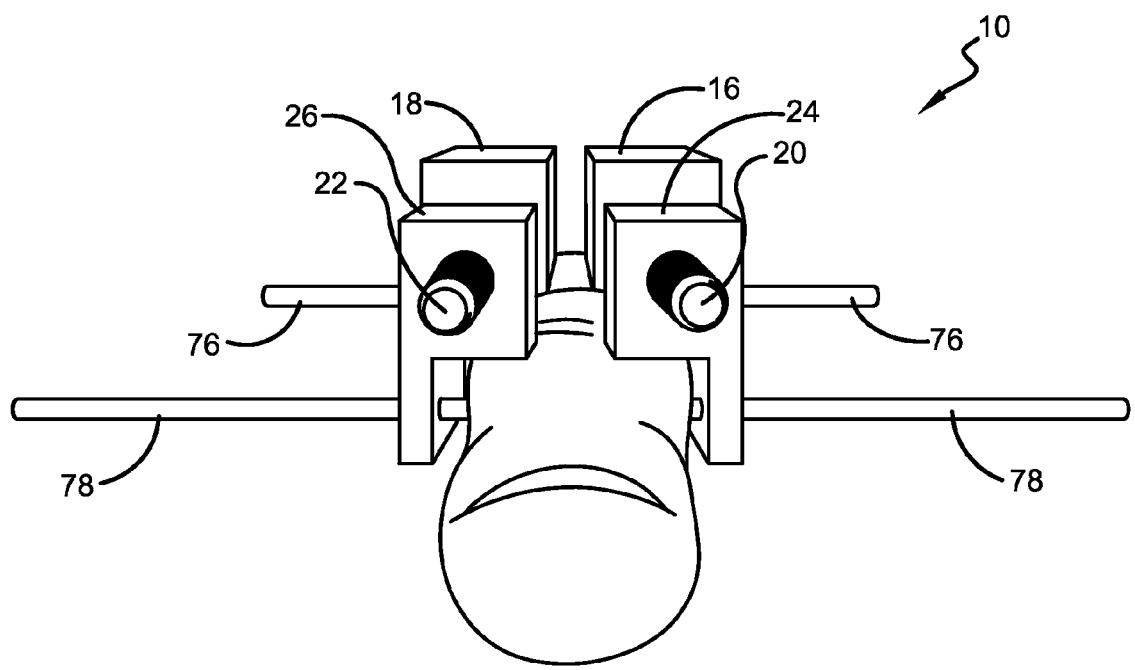
FIG. 4 is another front perspective view of the distractor of FIG. 1, as attached to a finger.
Figure 5:
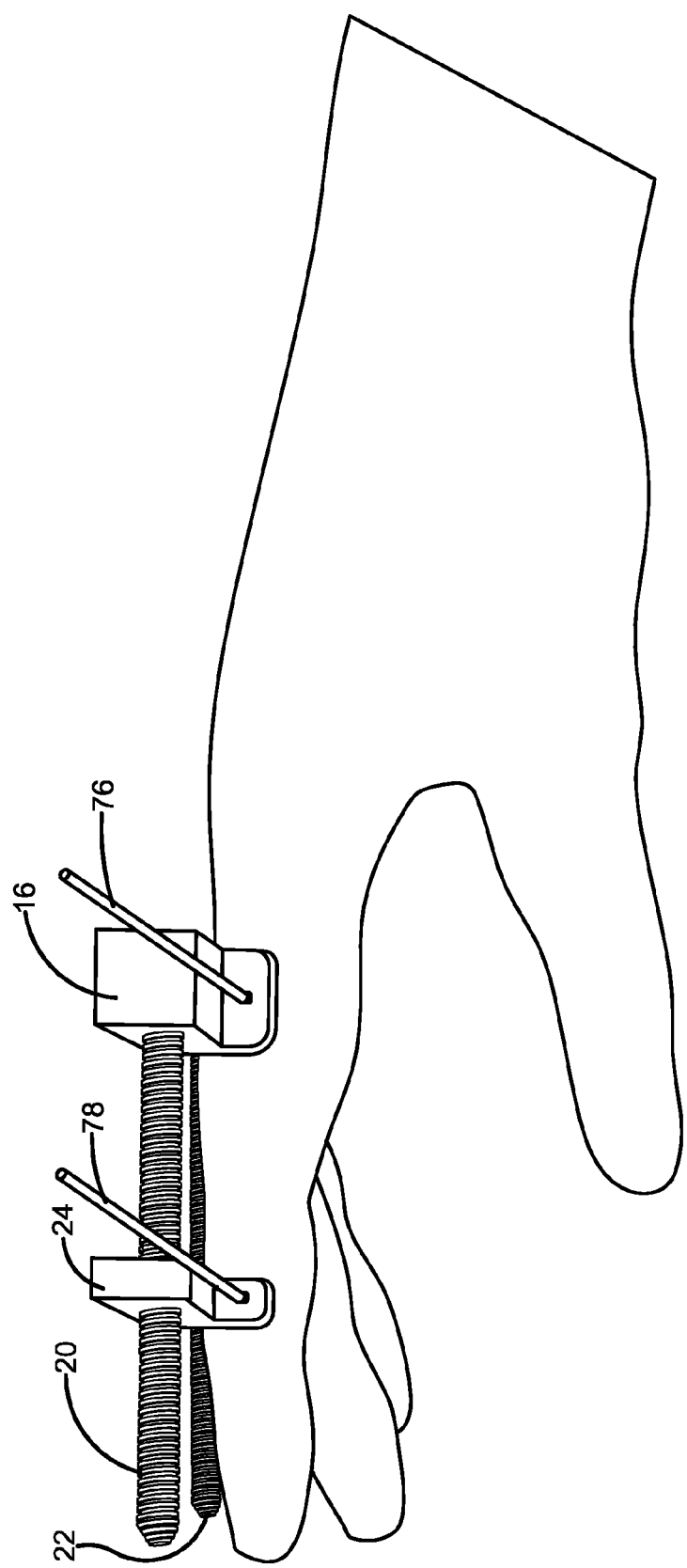
FIG. 5 is a side perspective view of the distractor of FIG. 1, as attached to a finger.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices are shown in block diagram form in order to facilitate a description thereof.

The present invention discloses an improved dynamic external distractor for the treatment of complex fracture luxations of the PIP of the hand. The objective of the device is to provide a simple, low cost solution for the treatment of fracture dislocations of the PIP. Another objective of the device is to permit standardization of treatment, by enabling surgeons to determine distraction forces, an important treatment parameter, which heretofore was impossible due to the limitations of devices described in prior art. Standardization will permit better patient outcomes than currently possible with existing systems.

Figure 6:
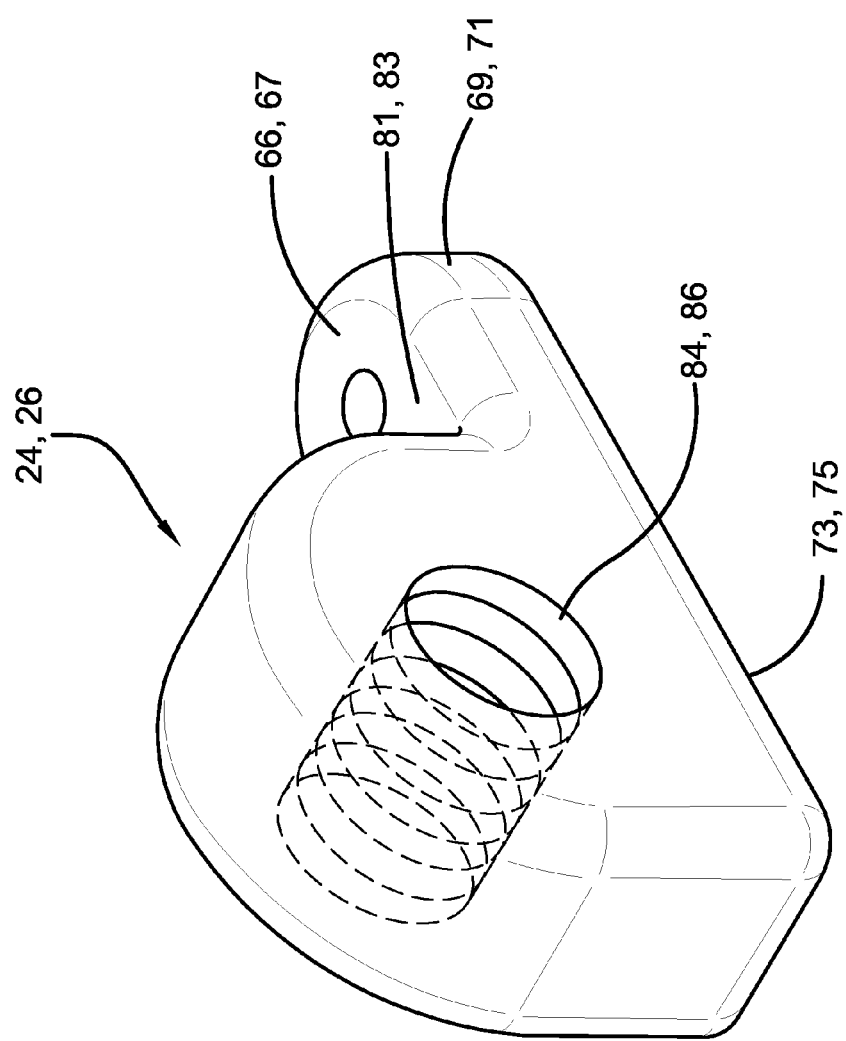
FIG. 6 shows multiple views of a distal guide block of the distractor of FIG. 1.
Figure 7:
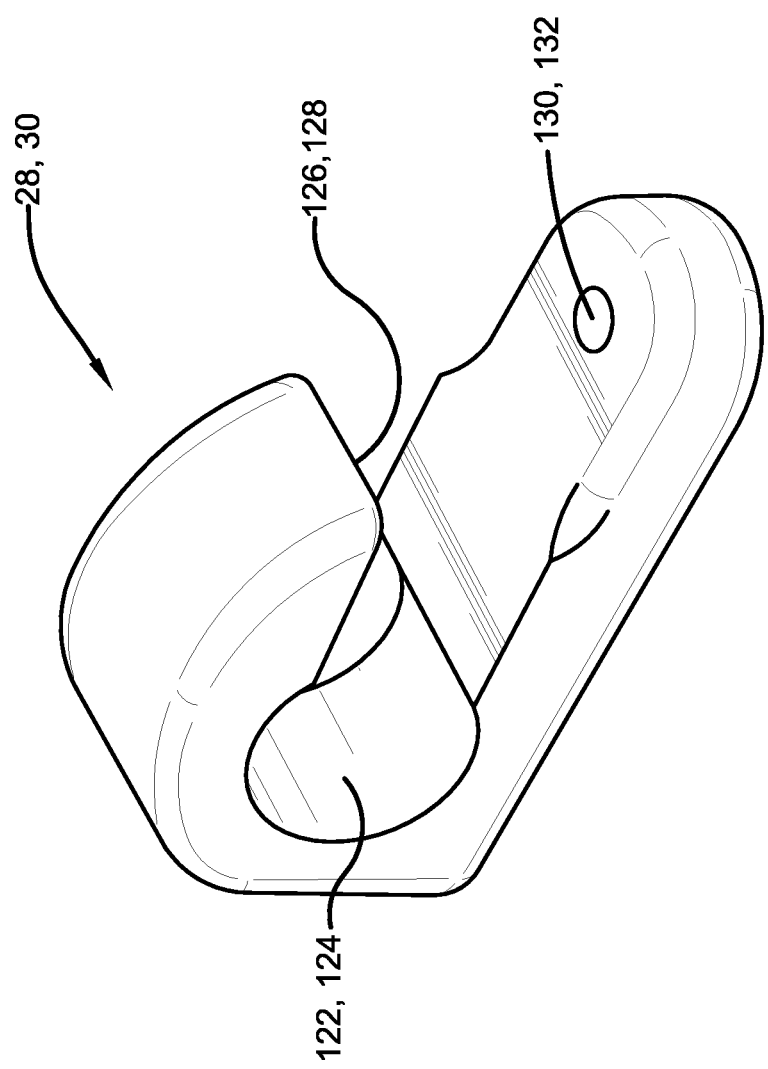
FIG. 7 shows multiple views of an optional alignment guide clip of the distractor of FIG. 1.
Figure 8:
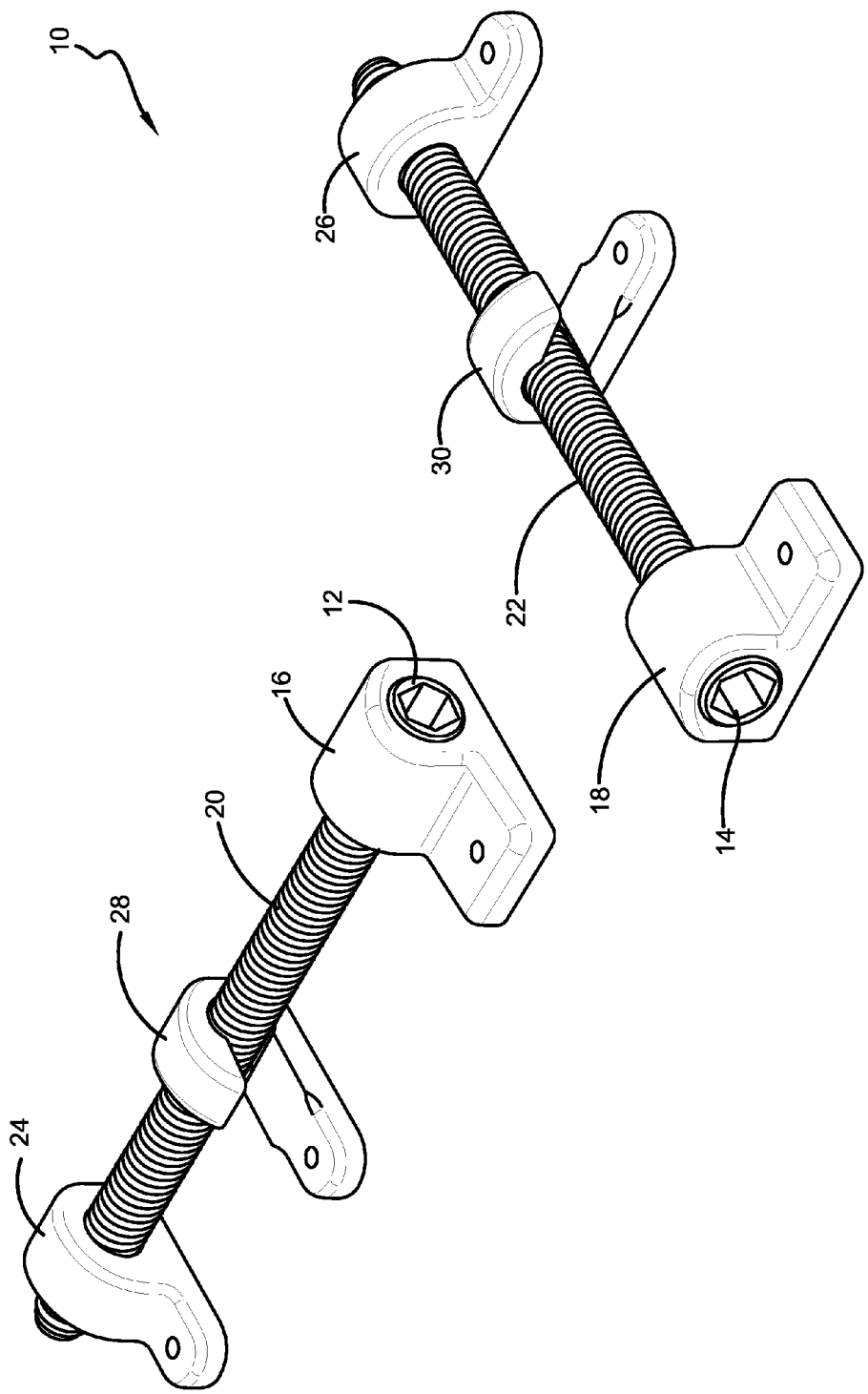
FIG. 8 is an assembly drawing of an assembly of a portion of the distractor of FIG. 1, including a threaded rod, proximal guide block, distal guide block, alignment guide clip and set screw.
Figure 11:
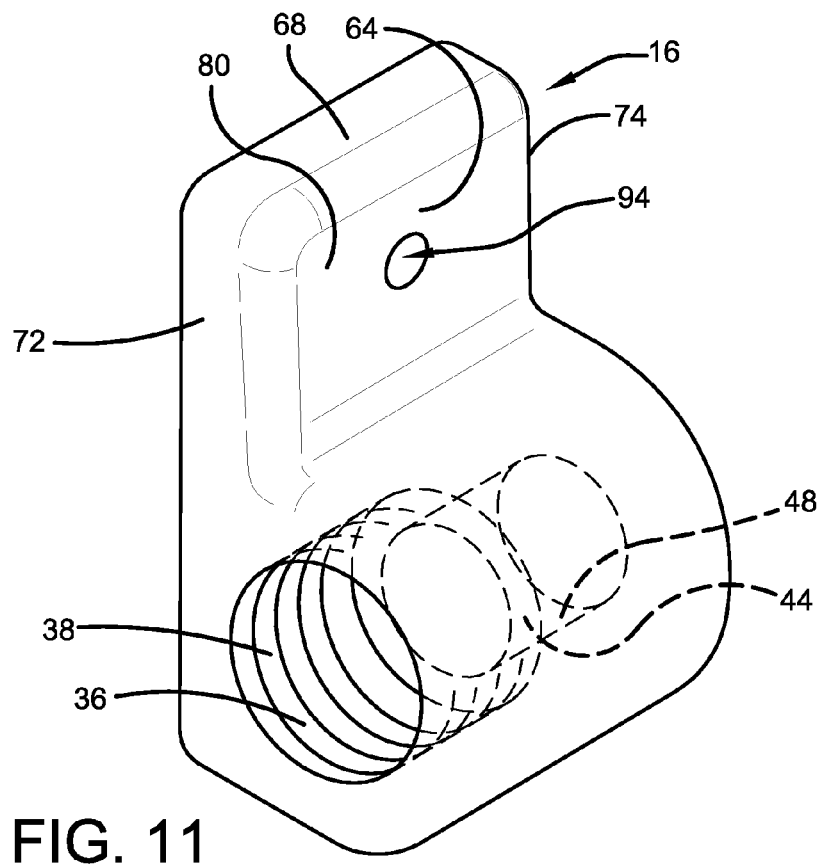
FIG. 11 shows multiple views of a left proximal guide block of the distractor of FIG. 1.
Figure 12:
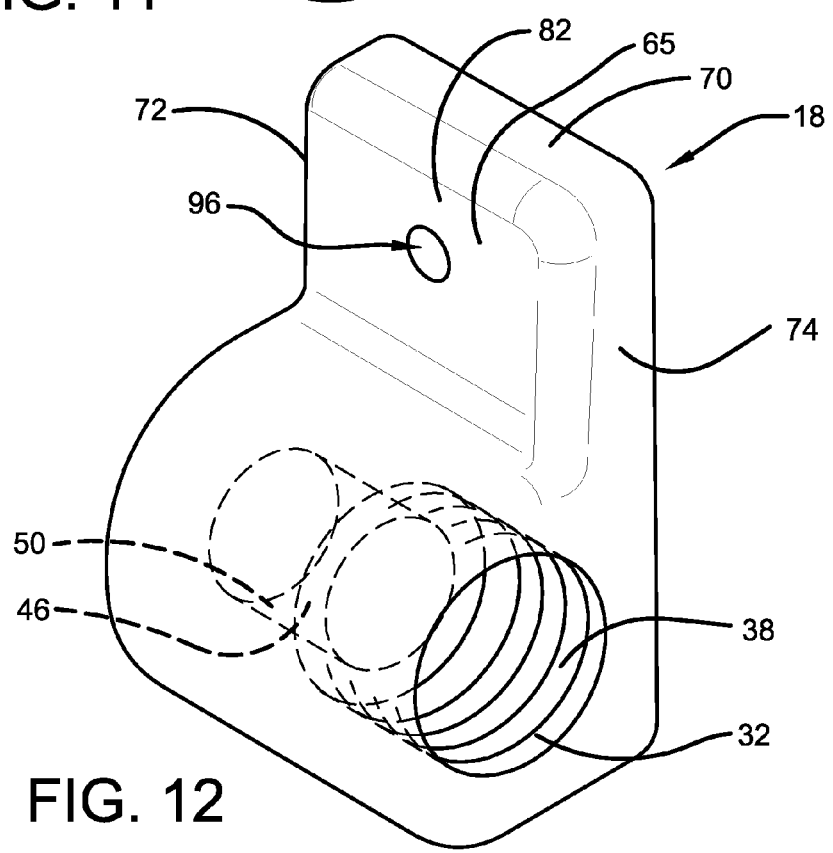
FIG. 12 shows multiple views of a right proximal guide block of the distractor of FIG. 1.

Referring now to the drawings wherein like part numbers refer to like elements throughout the several views, there is shown in FIGS. 1-5 a bilateral dynamic external distractor 10 for the treatment of complex fracture luxations of the PIP of the hand in accordance with an exemplary embodiment of the present invention, and FIGS. 6-12 disclose various components of the external distractor 10. The distractor 10 includes two setscrews 12, 14 (as shown in FIG. 9), one left proximal guide block 16 (as shown in FIGS. 8 and 11), one right proximal guide block 18 (as shown in FIGS. 8 and 12), two threaded rods 20, 22 (as shown in FIGS. 8 and 10), two distal guide blocks 24, 26 (as shown in FIGS. 6 and 8), and two optional alignment guide clips 28, 30 (as shown in FIGS. 7 and 8).

While the various components may be constructed of any material suitable for contact with the human body, the preferred materials are non-metallic, and radiolucent. During manufacture, the threaded rods 20, 22 are passed through a passage 32, 34 in the left proximal guide block 16 and the right proximal guide block 18. The passages 32, 34 each have one large diameter threaded hole 36, 38 (as shown in FIG. 11) to permit a raised flange 40, 42 (as shown in FIG. 10) on the threaded rods 20, 22 to enter. The threaded passages 32, 34 terminate in a wall 44, 46 through which is an unthreaded small passage 48, 50 which is slightly larger in diameter than the diameter of the threaded portions 52, 54 of the threaded rods 20, 22. The diameters of the raised flanges 40, 42 on the threaded rods 20, 22 are larger than the small passages 48, 50 and are prevented from continuing through the guide blocks 16, 18, by the guide block walls 44, 46. Setscrews 12, 14 or other suitable securing devices as is known in the art, are threaded into the passages 32, 34 and act to retain the threaded rods 20, 22 in place, while permitting them to rotate within the guide block 24, 26. The setscrews 12, 14 have cupped ends 56, 58 which, when threaded completely into passages 32, 34 are designed to bias against the proximal faces 60, 62 of the flanges 40, 42, locking the threaded rods 20, 22 in place and preventing them from moving or rotating. Further, the proximal guide blocks 16, 18 and the distal guide blocks 24, 26 have rounded edges to prevent injury to the patient.

A flat leg 64, 65 extends from each of the proximal guide blocks 16, 18. A flat leg 66, 67 extends from each of the distal guide blocks 24, 26. The lengths of the legs 64, 65 are sufficient to permit passages 32, 34, 48, 50 of the proximal guide blocks 16,18 to rise above the ulnar plane of the digit, when the base 68, 70 of the leg 64, 65 is parallel to the volar plane of the digit to be treated. The lengths of the legs 66, 67 are sufficient to permit passages 84, 96 of the distal guide blocks 26, 28 to rise above the ulnar plane of the digit, when the base 69, 71 of the leg 66, 67 is parallel to the volar plane of the digit to be treated.

The outside flat surfaces 72, 74, 73, 75 of the guide blocks 16, 18, 24, 26, respectively, are designed to rest against the lateral sides of the digit when attached to the K-wires 76, 78. Alternatively, the inside surface 80, 82, 81, 83 of the guide blocks 16, 18, 24, 26 may rest against the lateral sides of the treated digit. The distal guide blocks 24, 26 have the same cross section as the proximal guide blocks 16, 18 and are approximately half the width. They also have threaded passages 84, 86 designed to mate with the threaded portion 52, 54 of the threaded rods 20, 22. The distal guide blocks 24, 26 are threaded on to the threaded rods 20, 22 with the flat surface 73, 75 on the same side as the flat surface 72, 74 of the left and right proximal guide blocks 16, 18.

The rods 20, 22 and guide blocks 16, 18, 24, 26 are packaged pre-assembled, reducing procedure time in surgery. Further, placement of K-wires 76, 78 is according to standard technique as is known in the art. The proximal K-wire 76 is drilled through proximal interphalangeal bone 88 at the axis of rotation proximal to the joint. Placement of the distal K-wire 78 is parallel to, and in the same plane as the proximal K-wire 76, through the middle interphalangeal bone joint 90, slightly proximal to the distal interphalangeal joint 92. The proximal guide blocks 16, 18 and distal guide blocks 24, 26 of the left and right arms of the distractor 10 are adjusted so that the bottom alignment holes 94, 96 in each match the distance between the proximal and distal K-wires 76, 78. Adjustment is accomplished by rotation of the threaded rods 20, 22. The inner diameter of the alignment holes 94, 96 of the guide blocks 16, 18, 24, 26 are slightly larger than the outer diameter of the K-wires 76, 78, allowing the device to be slipped onto the K-wires 76, 78 on either side of the digit, with the threaded rods 20, 22 above the volar aspect of the digit. The larger diameter of the alignment holes 94, 96, also permits the device to rotate around the K-wires 76, 78 during active and passive motion of the digit. This prevents the K-wires 76, 78 from rotating inside the bone, thereby reducing the risk of pin-tract infection, a common complication of the prior art.

Once the flat legs 64, 65 of the proximal guide blocks 16, 18 are in contact with the digit, the K-wires 76, 78 may be cut and covered with K-wire caps (not shown) to retain the position of the blocks 16, 18 and to prevent soft tissue damage to the patient or clinician. While an accommodation at the distal end of the rods 20, 22 may be provided for a knurled knob or tool to accomplish rotation, the preferred embodiment has no such provision. This minimizes the potential of joint stiffness or other complications, which may result from excessive force applied to the digit. Distraction may then be achieved by manual clockwise rotation of the threaded rods 20, 22 of each arm between the thumb and forefinger at the distal ends 102, 104 of the threaded rods 20, 22 to prevent excessive stress to the ligaments. In the preferred embodiment, the threaded rods 20, 22 include an 8-32 pitch, such that a 360-degree clockwise rotation of the rod results in an increase of the distraction force by approximately 4.5 newtons (1 lb.). Further, 90 degree reference marks located on the distal faces of the left and right proximal guide blocks (16, 18) permit the surgeon to adjust the distraction force in increments of 1.1 (+/−0.2) newtons. Other suitable thread pitches as is known in the art may be selected at time of manufacture to achieve a finer or more course adjustment. A marked line 108, 110 on the longitudinal axis 110, 112 of the threaded rods 20, 22 can provide visual confirmation to the clinician of the distraction force applied, by counting the number of rotations of the rods 20, 22. In addition, horizontal marked lines 114, 116 along the length of the rods 20, 22, for example, one millimeter apart and perpendicular to the longitudinal axes 110, 112 of the rods 20, 22 permit the clinician to visualize the amount of distraction achieved at the joint (i.e., the amount of separation at the PIP articulation) without reference to fluoroscopy. This reduces the radiation exposure to patient and surgical staff.

A common complication of similar devices is ulnar or palmar luxation of the middle phalanx following distraction. Optional alignment guide clips 28, 30 are provided which may be press fit onto the threaded rods 20, 22 at any point between the proximal guide blocks 16, 18 and distal guide blocks 24, 26 to prevent luxation of the middle phalangeal bone (as shown in FIG. 8). The alignment clips 28, 30 are identical to the distal guide blocks 24, 26, with the exception that the passage 122, 124 (analogous to passages 48, 50) in the clips are not threaded and equivalent in diameter to the small passage 48, 50 of the proximal guide blocks 16, 18. In addition, a section of the arc 126, 128 below the passages 122, 124, slightly smaller than the diameter of the threaded portions 52, 54 of the rods 20, 22 are removed to permit the clips 28, 30 to be press fit onto the threaded rods 20, 22. Each clip 28, 30 has an alignment hole 130, 132, though which a third K-wire 138 may be passed. The third K-wire 138 is drilled though the middle phalanx 140, at a point distal to the PIP. The third K-wire 138 is placed though the alignment holes 130, 132 in the clips 28, 30 and the clips 28, 30 are slid along the axis of the K-wire 138 to the threaded rods 20, 22 where they are press fit onto the rods 20, 22. The middle phalanx 140 is thereby prevented from luxation. An additional feature of the clips 28, 30 is that, in conjunction with K-wires, bone fragments may be fixated to assist in healing of the fracture.

Furthermore, x-ray confirmation of distraction may be accomplished via lateral, ulnar and volar views. In as much as the device components are radiolucent, clear visualization may be made of all structures to ensure proper treatment of the injury. Once the surgeon is satisfied with the result, the threaded rods 20, 22 may be locked in place by tightening the retention set screws 12, 14 in the proximal guide blocks 16, 18 (as shown in FIG. 9). Clockwise rotation of the set screws 12, 14 forces the cupped surface 56, 58 of the set screws 12, 14 against the face 60, 62 of the threaded rods 20, 22, forcing it against the inner walls 44, 46 of the distal guide blocks 24, 26 thereby locking the threaded rods 20, 22 in place. Thus, the digit may be exercised under both active and passive motion as prescribed by the attending physician. Further, subsequent evaluation of clinical progress may be made without disassembly of the device. Relaxing of distraction may be accomplished by loosening the setscrews 12, 14 and rotation of the rods 20, 22 in a counter clockwise direction. The device 10 may be tensioned by reversing the process once the evaluation is complete.

An additional feature of the distractor 10 is the ability to achieve compression. K-wires may be placed on either side of a bone fracture and the device 10 may be applied as previously described. To achieve compression, rotation of the threaded rods 20, 22 in a counter clockwise direction will cause the bone segments to approximate one to the other.

Optionally, the threaded rods, 20, 22 may be hollow, rather than solid, as shown. This permits the insertion of a U-shaped stabilizer bar 142 (as shown in FIG. 1) to act as a bridge between the two sides of the distractor 10, providing lateral stability. The stabilizer bar 142 does not inhibit the threaded rods 20, 22 from rotating. Additionally, the stabilizer bar 142 provides additional strength to the threaded rods 20, 22 to prevent bending and breaking.

One or more recesses in the tips of the threaded rods 20, 22 may be provided such that the threaded rods 20, 22 are locked in place upon full insertion of the U-shaped stabilizer. This feature can be employed instead of or in conjunction with the locking set screws 12, 14.

Figure 13:
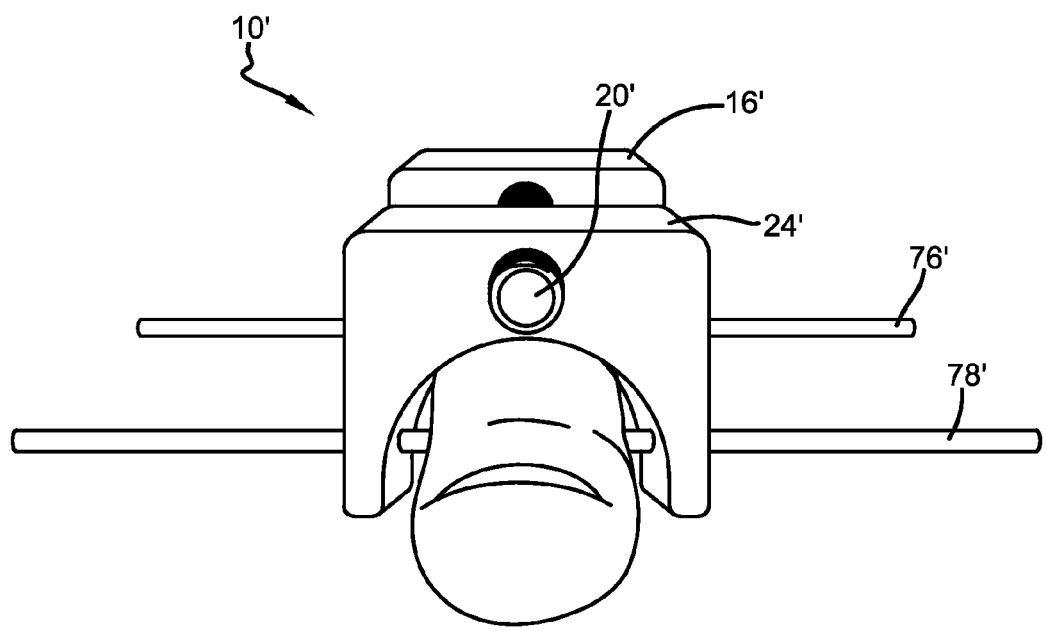
FIG. 13 is a front, perspective view of a bilateral distractor as attached to a finger in accordance with another exemplary embodiment of the present invention.
Figure 14:
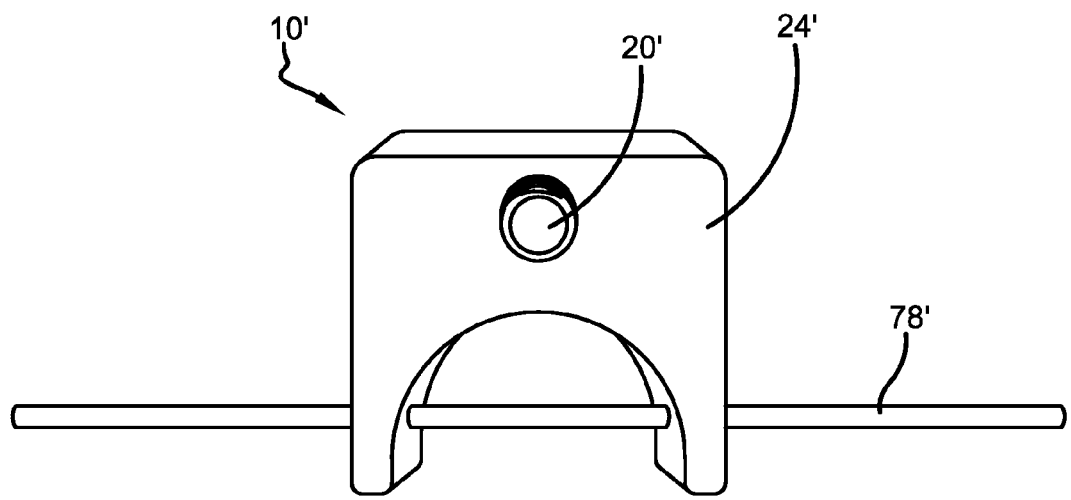
FIG. 14 is a front perspective view of a guide block, threaded rod and K-wire of the bilateral distractor of FIG. 13.
Figure 15:
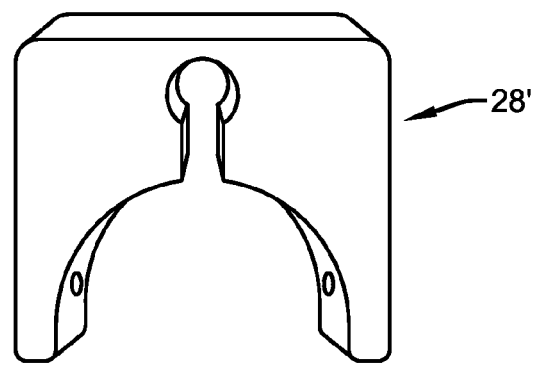
FIG. 15 is a front, perspective view of an optional guide clip of the bilateral distractor of FIG. 13.

As can be seen in FIGS. 13-15, in another exemplary embodiment of an external distractor 10', U-shaped proximal guide block 16' and U-shaped distal guide block 24' may be formed as arches (having two walls through which K-wires 76', 78' pass) with a provision for a single threaded rod 20' at the peak of the arch. In this configuration, the guide blocks 16', 24' are placed over the digit and the K-wires 76', 78' are drilled through the walls of the arches, proximal and distal to the PIP. Rotation of the threaded rod 20' will create the required distraction. Marks on the rod 20' will permit estimation of the force and distance of distraction. The proximal guide block 16' may have substantially the same locking feature utilizing setscrews as in the external distractor 10 of the first embodiment. The one-piece proximal guide block 16' and distal guide block 24' are positioned over the digit and the first K-wire 76' is drilled through side holes provided in the side walls of the proximal guide block 16', and through the arc of rotation, proximal to the PIP. The second K-wire 78' is positioned distal, along the middle phalanx, and the K-wire 78' is drilled through holes in the side walls of the distal guide block 24'. Distraction is achieved in the same manner as in the distractor 10' of the first embodiment, by clockwise rotation of the threaded rod 20'. Once distraction is achieved, the setscrew (similar to that of the first embodiment) on the proximal face of the proximal guide block is tightened to prevent the threaded rod 20' from rotating. A separate guide clip 28' (as shown in FIG. 15) can be snapped in position over the threaded rod 20' and a third K-wire can be drilled from one side to the other, through the middle phalanx to prevent luxation of the PIP (not shown in use, but used in a similar way to the guide clips 28, 30 of the distractor 10' of the first embodiment).

This device can also be used for fixation and compression of broken bones when no articulation is involved. For example, the guide blocks are positioned on either side of the fracture and K-wires are drilled through either one. Compression is achieved by counter-clockwise rotation of the threaded rod.

While this distractor is intended for use for treatment of small bones, it is also understood to be within the scope of the present invention that it may also be used in the treatment of long bones (where the various elements are scaled up in size, as necessary).

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:
1. A distractor comprising:
a left and a right proximal guide block;
a left and a right distal guide block, each having a threaded passage;
a first threaded rod extending between the right proximal guide block and the right distal guide block;
a second threaded rod extending between the left proximal guide block and the left distal guide block;

a first wire extending between the left and right proximal guide blocks;

a second wire extending between the left and right distal guide blocks;

whereby rotation of the first and second threaded rods causes the left and right distal guide blocks to move relative to the left and right proximal guide blocks along an axis of the first and second threaded rods; and a left alignment guide clip, a right alignment guide clip and a third wire extending between the left and right alignment guide clips; whereby each one of the alignment guide clips is press fit onto a respective threaded rod at a location on the threaded rod between a respective proximal guide block and a respective distal guide block; at least one set screw secured in each of the left and right distal guide blocks.

2. The distractor of claim 1, whereby in a first position, the at least one set screw acts to retain the respective threaded rod in place while permitting the threaded rod to rotate, and in a second position, the at least one set screw locks the respective threaded rod to prevent rotation of the respective threaded rod.

3. The distractor of claim 1, wherein each of the first and second threaded rods terminates in threads at a first end and a flat circular flange at a second end, and wherein a diameter of the second end is larger than a diameter of the first end of the first and second threaded rods.

4. The distractor of claim 1, further comprising vertical markings on the first and second threaded rods to show a user relative rotation of the first and second threaded rods.

5. The distractor of claim 1, further comprising horizontal markings on the first and second threaded rods to show a user relative rotation of the first and second threaded rods.

6. The distractor of claim 1, wherein the first and second threaded rods are hollow to permit the insertion of a U-shaped stabilizer bar which acts as a bridge between two sides of the distractor providing lateral stability; and wherein the U-shaped stabilizer bar does not prevent the first and second threaded rods from rotating.

7. The distractor of claim 1 wherein an increase of distraction force approximately between 2 and 10 newtons is created with each 360-degree rotation of the first and second threaded rods depending on thread pitch.

8. A distractor comprising:
a left and a right proximal guide block;
a left and a right distal guide block, each having a threaded passage;
a first threaded rod extending between the right proximal guide block and the right distal guide block;
a second threaded rod extending between the left proximal guide block and the left distal guide block;
a first wire extending between the left and right proximal guide blocks;
a second wire extending between the left and right distal guide blocks;
a U-shaped stabilizer bar; and
whereby rotation of the first and second threaded rods causes the left and right distal guide blocks to move relative to the left and right proximal guide blocks along an axis of the first and second threaded rods; wherein the first and second threaded rods are hollow to permit the insertion of the U-shaped stabilizer bar which acts as a bridge between the two sides of the distractor providing lateral stability; and wherein the U-shaped stabilizer bar does not prevent the first and second threaded rods from rotating.

9. The distractor of claim 8, further comprising at least one set screw secured in each of the left and right distal guide blocks; whereby in a first position, the at least one set screw acts to retain the respective threaded rod in place while permitting the threaded rod to rotate, and in a second position, the at least one set screw locks the respective threaded rod to prevent rotation of the respective threaded rod.

10. The distractor of claim 8, wherein each of the first and second threaded rods terminates in threads at a first end and a flat circular flange at a second end, and wherein a diameter of the second end is larger than a diameter of the first end of the first and second threaded rods.

11. The distractor of claim 8, further comprising vertical markings on the first and second threaded rods to show a user relative rotation of the first and second threaded rods.

12. The distractor of claim 8, further comprising horizontal markings on the first and second threaded rods to show a user relative rotation of the first and second threaded rods.

13. The distractor of claim 8 wherein an increase of distraction force approximately between 2 and 10 newtons is created with each 360-degree rotation of the first and second threaded rods.

\* \* \* \* \*